United States Patent [19]

Jinnai et al.

[11] 4,058,475

[45] Nov. 15, 1977

[54] LIQUID CRYSTAL COMPOSITIONS CONTAINING CYANOCINNAMIC ACID ESTERS

[75] Inventors: Toshio Jinnai; Goro Matusmoto; Kazuhito Iwasaki, all of Odawara, Japan

[73] Assignee: Dai Nippon Toryo Co., Ltd., Osaka, Japan

[21] Appl. No.: 692,561

[22] Filed: June 3, 1976

[30] Foreign Application Priority Data

| June 5, 1975 | Japan | 50-68022 |
| June 12, 1975 | Japan | 50-71278 |
| Aug. 18, 1975 | Japan | 50-100001 |
| Feb. 12, 1976 | Japan | 51-14323 |

[51] Int. Cl.² .................. C07C 121/75; C09K 3/34
[52] U.S. Cl. ..................... 252/299; 260/465 D; 350/160 LC
[58] Field of Search ................... 260/465 D; 252/299

[56] References Cited

U.S. PATENT DOCUMENTS 3,927,066  12/1975  Scherrer et al. ............... 260/465 D

*Primary Examiner*—Dolph H. Torrence

[57] ABSTRACT

Liquid crystalline p-cyanocinnamic acid p'-n-alkoxyphenyl esters, and nematic liquid crystal compositions containing the same, useful for electro-optical devices, are described.

6 Claims, 3 Drawing Figures

A: p-CYANOCINNAMIC ACID p'-n-HEPTYLOXYPHENYL ESTER
B: p-CYANOCINNAMIC ACID p'-n-BUTYLPHENYL ESTER

A: p-CYANOCINNAMIC ACID p'-n-HEPTYLOXYPHENYL ESTER
B: p-n-BUTYLOXYCINNAMIC ACID p'-CYANOPHENYL ESTER

A: p-CYANOCINNAMIC ACID p'-n-HEPTYLOXYPHENYL ESTER
B: p-n-BUTYLCINNAMIC ACID p'-CYANOPHENYL ESTER

LIQUID CRYSTAL COMPOSITIONS CONTAINING CYANOCINNAMIC ACID ESTERS

BACKGROUND OF THE INVENTION

1. Field of the Invention

This invention relates to liquid crystalline cinnamic acid esters, and more particularly to liquid crystalline p-cyanocinnamic acid p'-n-alkoxyphenyl esters and nematic liquid crystal compositions containing the same.

2. Description of the Prior Art

Nematic liquid crystal compounds of nematic liquid crystal compositions have recently come into wide use in display devices and light attenuators in electronic and optical instruments because of their useful physical and chemical characteristics. Nematic liquid crystal compounds and compositions can be divided into two groups according to their dielectric anisotropy. Falling in one group are the Nn-liquid crystal compounds or Nn-liquid crystal compositions which have negative dielectric anisotropy, and falling in the other are the Np-liquid crystal compounds or Np-liquid crystal compositions which have positive dielectric anisotropy.

As is well known in the art, nematic liquid crystal compounds and compositions are used in electro-optical display elements in which the optical appearance thereof is changed by application and removal of an electric field. One example of a liquid crystal display element is the DSM (Dynamic Scattering Mode) type display element, and another example thereof is the FEM (Field Effect Mode) type display element.

From the viewpoint of practical use, nematic liquid crystal compound or composition is preferably in the mesomorphic state over a wide temperature range, particularly one which covers low temperatures.

SUMMARY OF THE INVENTION

The primary object of the present invention is to provide novel nematic liquid crystalline cinnamic acid esters and nematic liquid crystal compositions containing the same.

Another object of the present invention is to provide nematic liquid crystal compounds and compositions which are in the mesomorphic state over a wide range of temperatures.

The above objects are accomplished in accordance with the present invention which provids liquid crystalline p-cyanocinnamic acid p'-n-alkoxyphenyl esters of the formula

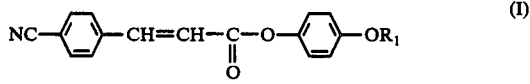

wherein $R_1$ is straight-chain alkyl of 4 to 8 carbon atoms, and also provides nematic liquid crystal compositions containing said esters.

DESCRIPTION OF PREFERRED EMBODIMENTS

Figure 1:
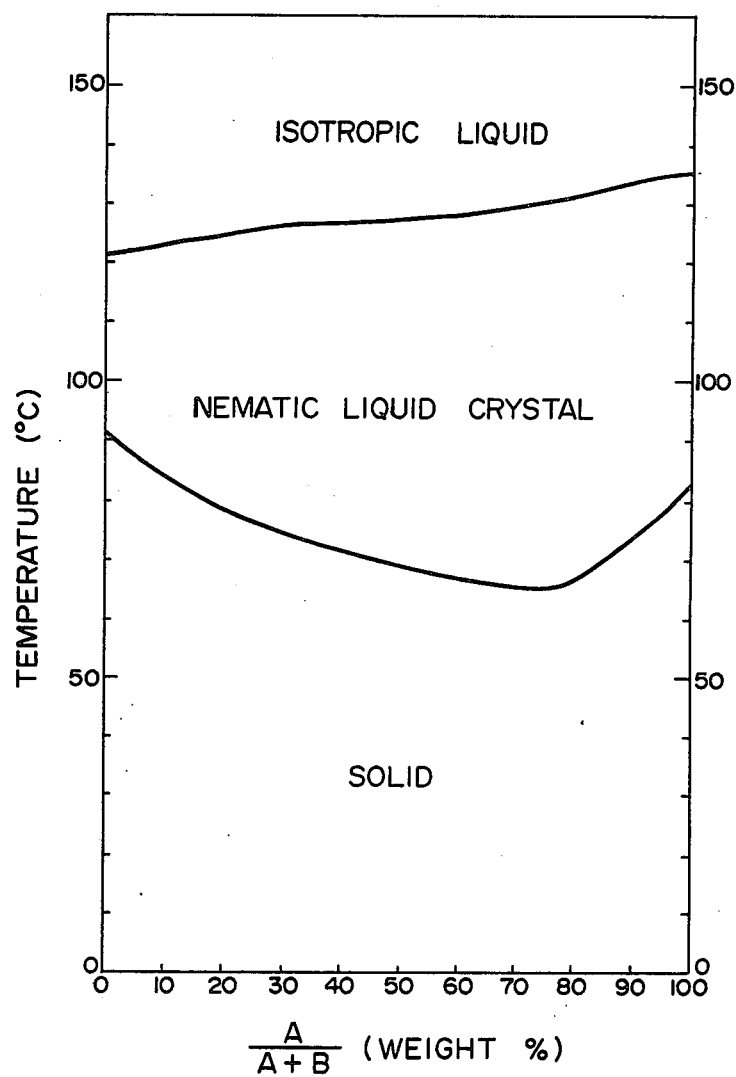
FIGS. 1, 2 and 3 are phase diagrams of preferred embodiments of the nematic liquid crystal compositions in accordance with the present invention.

The straight-chain alkyl group indicated by $R_1$ in the foregoing formula (I) is, for example, n-butyl group, n-pentyl group, n-hexyl group, n-heptyl group or n-octyl group.

Followings are some examples of the structure of the p-cyanocinnamic acid p'-n-alkoxyphenyl esters of formula (I)

Compound (1)

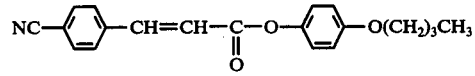

Compound (2)

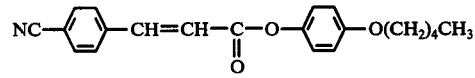

Compound (3)

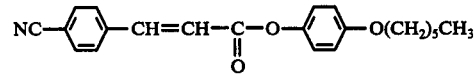

Compound (4)

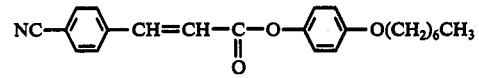

Compound (5)

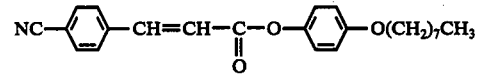

The above p-cyanocinnamic acid p'-n-alkoxyphenyl esters are all novel Np-liquid crystal compounds per se. The transition points from solid to nematic phase (KN point) and from nematic to isotropic liquid phase (NI point) of each compound are shown in Table 1 for the respective compounds.

Table 1

| Compound | KN point (° C) | NI point (° C) |
| --- | --- | --- |
| (1) | 104.5 | 146 |
| (2) | 89 | 136.5 |
| (3) | 74 | 139.5 |
| (4) | 82 | 135.5 |
| (5) | 98 | 136 |

The p-cyanocinnamic acid p'-n-alkoxyphenyl esters of formula (I) can be prepared by the interaction of p-n-alkoxyphenol of the formula

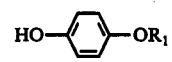 (Ia)

wherein $R_1$ is as previously described and p-cyanocinnamic acid chloride.

This reaction is represented by the following reaction formula.

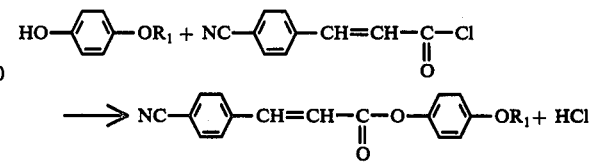

Since this reaction entails removal of a hydrogen chloride, it is preferably carried out in the presence of an agent for promoting the removal of hydrogen chloride such as pyridine or triethylamine. Though not always necessary, the reaction should preferably be carried out at under heating. This reaction can be carried out without solvent but is preferably carried out in a proper inert solvent such as benzene to dissolve the starting materials and prevent rapid reaction.

The starting material, p-cyanocinnamic acid chloride, can be easily prepared, for instance, by heating and stirring p-cyanobenzaldehyde and malonic acid in the presence of pyridine and piperidine, and chlorinating the resulting p-cyanocinnamic acid with thionyl chloride.

The p-cyanocinnamic acid p'-n-alkoxyphenyl esters of this invention, as described above, are Np-liquid crystal compounds and are characterized by a remarkably wide mesomorphic range. Furthermore, by mixing two or more of these esters together or mixing one or more of these esters with other cinnamic acid esters, Np-liquid crystal compositions having an even wider mesomorphic range can be prepared. Said other cinnamic acid esters which can be added to the p-cyanocinnamic acid p'-n-alkoxyphenyl esters of formula (I) are selected from the group consisting of p-cyanocinnamic acid p'-n-alkylphenyl esters, p-n-alkoxycinnamic acid p'-cyanophenyl esters, and p-n-alkylcinnamic acid p'-cyanophenyl esters which are represented by the following formulae (II), (III) and (IV), respectively.

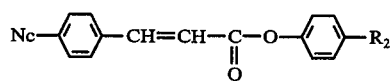 (II)

wherein $R_2$ is straight-chain alkyl of 3 to 8 carbon atoms,

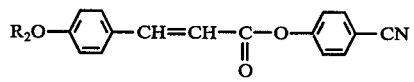 (III)

wherein $R_2$ is as previously described, and

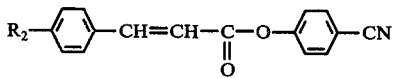 (IV)

wherein $R_2$ is as previously described.

The p-cyanocinnamic acid p'-n-alkylphenyl esters, p-n-alkoxycinnamic acid p'-cyanophenyl esters, and p-n-alkylcinnamic acid p'-cyanophenyl esters represented by above formulae (II), (III) and (IV) are Np-liquid crystal compounds per se. Several examples of these esters, and the KN points and NI points thereof are described hereinbelow and in Tables 2, 3 and 4.

p-cyanocinnamic acid p'-n-alkylphenyl esters
Compound (6)

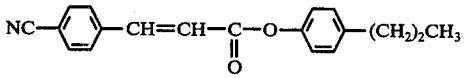

Compound (7)

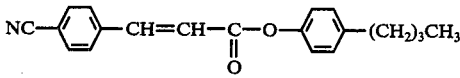

Compound (8)

-continued

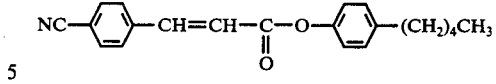

Compound (9)

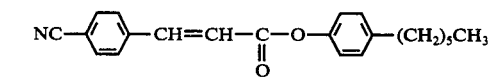

Compound (10)

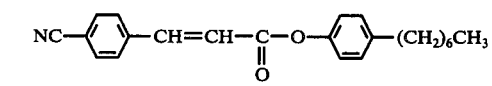

Compound (11)

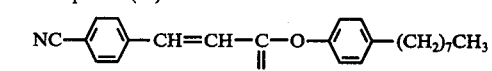

Table 2

| Compound | KN point (° C) | NI point (° C) |
|----------|----------------|----------------|
| (6)  | 122.5 | 131   |
| (7)  | 91    | 121   |
| (8)  | 86.5  | 125   |
| (9)  | 77    | 117.5 |
| (10) | 76    | 118.5 |
| (11) | 79.5  | 114   | p-n-alkoxycinnamic acid p'-cyanophenyl esters
Compound (12)

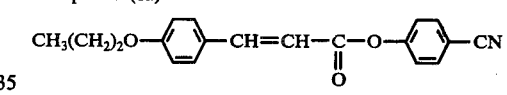

Compound (13)

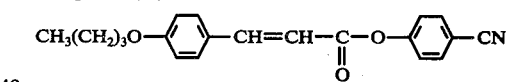

Compound (14)

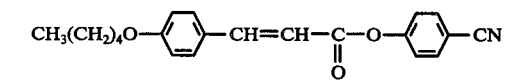

Compound (15)

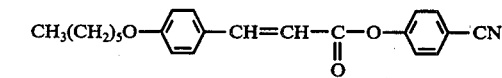

Compound (16)

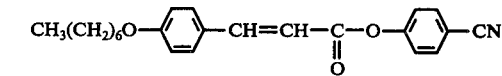

Compound (17)

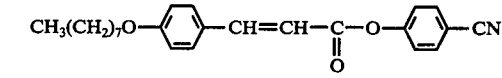

Table 3

| Compound | KN point (° C) | NI point (° C) |
|----------|----------------|----------------|
| (12) | 111.5 | 143   |
| (13) | 89    | 141.5 |
| (14) | 83.5  | 133   |
| (15) | 73    | 134   |
| (16) | 72    | 128   |
| (17) | 85    | 127.5 | p-n-alkylcinnamic acid p'-cyanophenyl esters

Compound (18)
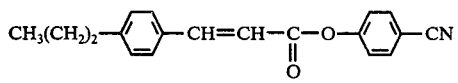

Compound (19)
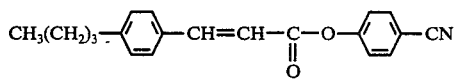

Compound (20)
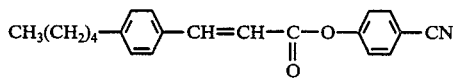

Compound (21)
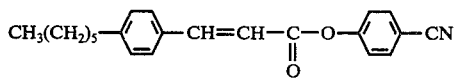

Compound (22)
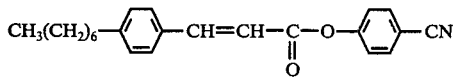

Compound (23)
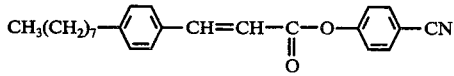

Table 4

| Compound | KN point (° C) | NI point (° C) |
|---|---|---|
| (18) | 103 | 132 |
| (19) | 87.5 | 119.5 |
| (20) | 76.5 | 124.5 |
| (21) | 73 | 106.5 |
| (22) | 61.5 | 116.5 |
| (23) | 66 | 110 |

The nematic liquid crystal compositions of this invention are Np-liquid crystal compositions and are characterized in that at least one of the p-cyanocinnamic acid p'-n-alkoxyphenyl esters of formula (I) is contained therein. There are no critical limits or requirements in the number and mixing ratio of the compounds constituting the compositions.

The nematic liquid crystal compositions in accordance with the present invention can be prepared by weighing the respective compounds and heating the same up to about 180° C in the presence of nitrogen gas to change it into an isotropic liquid, and then sufficiently stirring the same to mix the compounds. Alternatively, the compounds may be mixed first, and then heated and stirred.

Np-liquid crystal compositions containing cinnamic esters in accordance with this invention are characterized by a wide mesomorphic range covering low temperatures. The mesomorphic range of the Np-liquid crystal compositions consisting of several Np-liquid crystal compounds is wider than that of the respective compounds, and is advantageously shifted to the low temperature side. This is apparent from the examples described below and the drawing. The Np-liquid crystal compositions in accordance with the present invention are useful as liquid crystal materials for FEM type display devices.

EXAMPLE 1

0.2mol of p-cyanobenzaldehyde and 0.3mol of malonic acid were dissolved in 80ml of pyridine at room temperature, and 30 drops of piperidine were added thereto. The mixture was heated and stirred for 4 hours at about 100° C. After the reaction, the solution was poured slowly into dilute hydrochloric acid (250ml hydrochloric acid/250g water). Then, the resulting white precipitate was separated by filtering and washed with dilute hydrochloric acid and water, and was recrystallized by use of glacial acetic acid to obtain p-cyanocinnamic acid. 0.3mol of thionyl chloride was added to 0.1mol of the p-cyanocinnamic acid and the mixture was heated and stirred at about 80° C for 3 hours. An excess thionyl chloride was then removed under reduced pressure to obtain p-cyanocinnamic acid chloride.

0.02mol of p-cyanocinnamic acid chloride obtained in the above process and 0.02mol of p-n-butyloxyphenol were added to 50ml of benzene, and 50ml of pyridine was slowly dropped thereinto. Thereafter, the mixture was heated and stirred at about 60° C for 3 hours. After the reaction, 100ml of benzene was added to the mixture. And then the mixture was washed with dilute hydrochloric acid, aqueous sodium hydroxide solution and water, and the organic layer thereof was dried by use of sodium sulfate anhydride. After removal of sodium sulfate by filtering, benzene was removed under reduced pressure and the residue was recrystallized in ethanol, whereby there were obtained p-cyanocinnamic acid p'-n-butyloxyphenyl esters (Compound (1)).

By using p-n-pentyloxyphenol, p-n-hexyloxyphenol, p-n-heptyloxyphenol and p-n-octyloxyphenol instead of p-n-butyloxyphenol in the above process, there were obtained Compounds (2), (3), (4) and (5), respectively.

The p-cyanocinnamic acid p'-n-alkoxyphenyl ester thus prepared was confirmed to be the object compound by infra-red absorption spectroscopy, gas chromatography and mass spectrometers.

EXAMPLE 2

Equal weight parts of Compounds (1) and (2) were maintained at 180° C until they melted into isotropic liquid, and were then mixed and stirred to obtain a Np-liquid crystal composition having a mesomorphic range of 91.5° to 142° C.

In a similar manner, by mixing more than one kind of p-cyanocinnamic acid p'-n-alkoxyphenyl esters, various Np-liquid crystal compositions were obtained. The mesomorphic range of the Np-liquid crystal compositions is shown in Table 5.

Table 5

| Constituent Compounds and Mixing Weight Ratio | KN point (° C) | NI point (° C) |
|---|---|---|
| (1) : (2) = 1 : 1 | 91.5 | 142 |
| (1) : (3) = 1 : 1 | 80 | 142 |
| (1) : (4) = 1 : 1 | 76.5 | 139.5 |
| (1) : (5) = 1 : 1 | 66 | 139 |
| (2) : (3) = 1 : 1 | 70.5 | 136 |
| (2) : (4) = 1 : 1 | 61 | 136.5 |
| (2) : (5) = 1 : 1 | 64 | 135.5 |
| (3) : (4) = 1 : 1 | 78 | 138 |
| (3) : (5) = 1 : 1 | 73.5 | 135.5 |
| (4) : (5) = 1 : 1 | 85 | 136 |
| (1) : (2) : (5) = 1 : 1 : 1 | 64 | 137.5 |
| (1) : (3) : (5) = 1 : 1 : 1 | 57 | 138 |
| (1) : (4) : (5) = 1 : 1 : 1 | 66 | 137.5 |
| (1) : (2) : (4) = 1 : 1 : 1 | 64 | 137 |
| (2) : (3) : (4) = 1 : 1 : 1 | 59 | 137 |
| (2) : (3) : (5) = 1 : 1 : 1 | 60 | 136.5 |

Table 5-continued

| Constituent Compounds and Mixing Weight Ratio | KN point (° C) | NI point (° C) |
|---|---|---|
| (2) : (4) : (5) = 1 : 1 : 1 | 66 | 135 |

As shown in Table 5, the Np-liquid crystal compositions in accordance with this invention have a wide mesomorphic range. The mesomorphic range of the compositions is generally wider than that of the Np-liquid crystal compounds constituting the compositions, and is shifted toward the lower temperature side.

EXAMPLE 3

Equal weight parts of Compounds (3) and (9) were separately heated up to 180° C until they melted into isotropic liquids. By stirring and mixing the liquids together, Np-liquid crystal composition having a mesomorphic range of 63° to 128.5° C was obtained. Similarly, by mixing at least one of the p-cyanocinnamic acid p'-n-alkoxyphenyl esters represented by formula (I) and at least one of the esters represented by formulae (II), (III) and (IV), various kinds of Np-liquid crystal compositions were obtained. The mesomorphic range of the compositions thus obtained is shown in Table 6.

Figure 2:
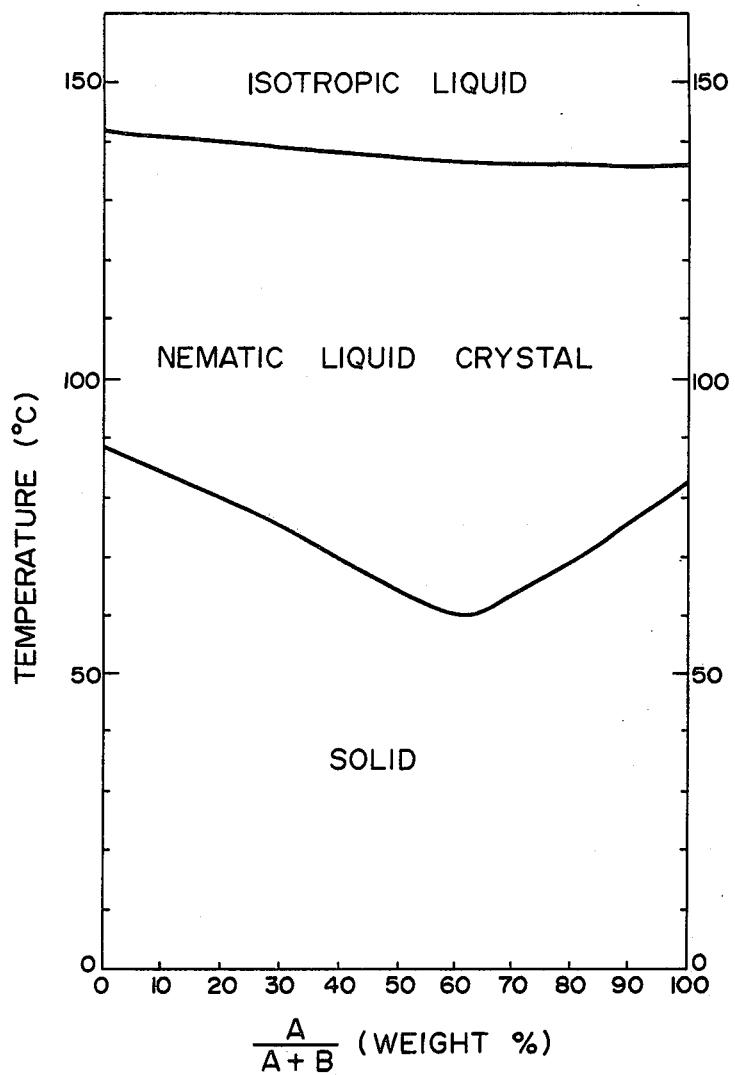
Figure 3:
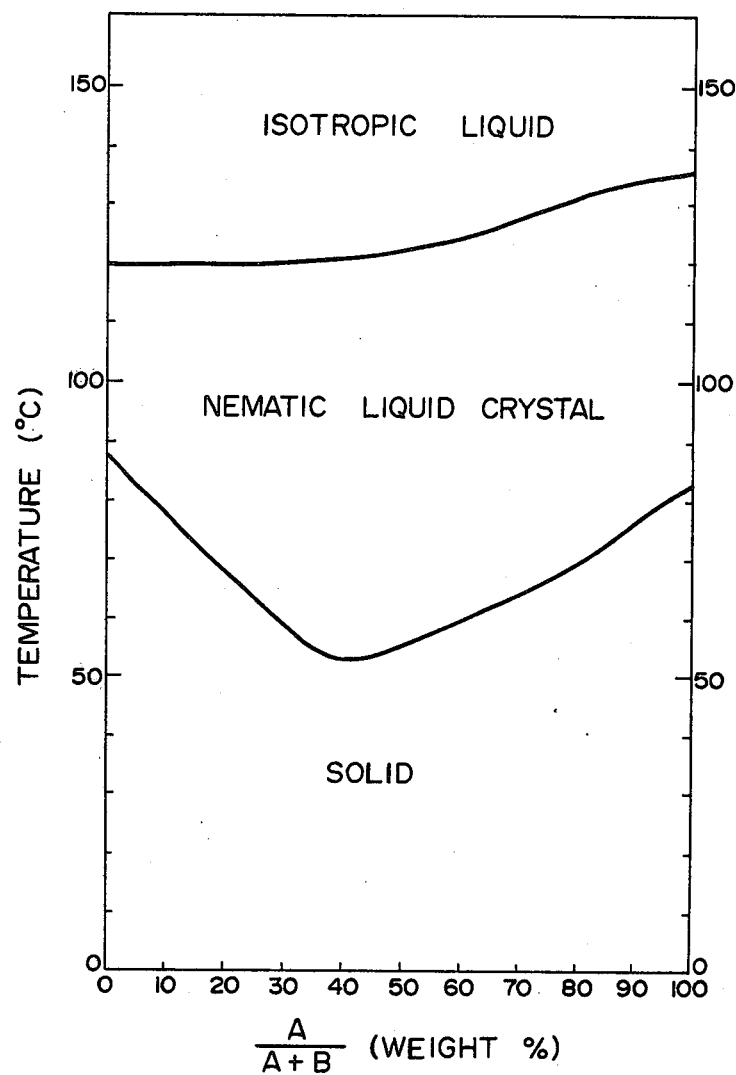

As shown in Table 6 and FIGS. 1 to 3, the Np-liquid crystal compositions in accordance with this invention have a markedly wide mesomorphic range.

Phase diagrams of the Np-liquid crystal compositions of this invention prepared by mixing Compounds (4) and (7), Compounds (4) and (13), and Compounds (4) and (19) are shown in FIGS. 1, 2 and 3, respectively.

Table 6

| NO. | Constituent Compounds and Mixing Weight Ratio | KN point (° C) | NI point (° C) |
|---|---|---|---|
| 1 | (3):(11)=1:1 | 65.5 | 127.5 |
| 2 | (2):(14)=1:1 | 65 | 131.5 |
| 3 | (3):(15)=1:1 | 60 | 131.5 |
| 4 | (3):(16)=1:1 | 49 | 132 |
| 5 | (1):(19)=1:1 | 65 | 126 |
| 6 | (2):(20)=1:1 | 58.5 | 124 |
| 7 | (3):(21)=1:1 | 56.5 | 121 |
| 8 | (4):(22)=1:1 | 39.5 | 122 |
| 9 | (5):(23)=1:1 | 57 | 119.5 |
| 10 | (3):(22)=1:1 | 47.5 | 122 |
| 11 | (4):(20)=1:1 | 53.5 | 121.5 |
| 12 | (4):(21)=1:1 | 56.5 | 119.5 |
| 13 | (4):(22)=1:2 | 46 | 116 |
| 14 | (3):(22)=1:2 | 47.5 | 118.5 |
| 15 | (2):(9):(10)=1:1:1 | 65.5 | 125.5 |
| 16 | (3):(9):(11)=1:1:1 | 52 | 122.5 |
| 17 | (2):(14):(16)=1:1:1 | 48 | 131.5 |
| 18 | (2):(15):(16)=1:1:1 | 51.5 | 130 |
| 19 | (3):(15):(16)=1:1:1 | 48.5 | 130 |
| 20 | (4):(19):(22)=1:1:1 | 30 | 116 |
| 21 | (4):(20):(22)=1:1:1 | 38.5 | 118.5 |
| 22 | (3):(20):(22)=1:1:1 | 41.5 | |
| 23 | (3):(21):(23)=1:1:1 | 43.5 | 117 |
| 24 | (2):(14):(15):(16)=1:1:1:1 | 46 | 130 |
| 25 | (3):(14):(15):(16)=1:1:1:1 | 43 | 129.5 |
| 26 | (4):(14):(15):(16)=1:1:1:1 | 48 | 129.5 |
| 27 | (2):(19):(20):(22)=1:1:1:1 | 37 | 113 |
| 28 | (3):(19):(20):(22)=1:1:1:1 | 35 | 115 |
| 29 | (3):(19):(21):(23)=1:1:1:1 | 19 | 111 |
| 30 | (4):(19):(20):(22)=1:1:1:1 | 35.5 | 112 |
| 31 | (4):(19):(21):(23)=1:1:1:1 | 17 | 110 |
| 32 | (2):(4):(14):(15):(16) =1:1:2:2:2 | 41 | 129 |
| 33 | (3):(4):(14):(15):(16) =1:1:2:2:2 | 44.5 | 129 |
| 34 | (3):(4):(19):(21):(22) =1:1:2:2:2 | 23 | 113 |
| 35 | (3):(4):(19):(21):(23) =1:1:2:2:2 | 21 | 111.5 |
| 36 | (1):(5):(19):(21):(23) =1:1:2:2:2 | 14 | 111.5 |
| 37 | (2):(4):(19):(20):(22) =1:1:2:2:2 | 23 | 114.5 |
| 38 | (2):(7):(19):(22) =1:0.72:0.92:1.36 | 20 | 115 |
| 39 | (3):(7):(19):(22) =1:0.72:0.92:1.36 | 19 | 115.5 |
| 40 | (4):(7):(19):(22) =1:0.72:0.92:1.36 | 32 | 115 |
| 41 | (2):(7):(9):(19):(20):(22) =1:0.7:0.6:0.9:0.6:1.2 | 21 | 114.5 |
| 42 | (3):(7):(9):(19):(20):(22) =1:0.7:0.6:0.9:0.6:1.2 | 15 | 113 |
| 43 | (4):(7):(9):(19):(20):(22) 1:0.7:0.6:0.9:0.6:1.2 | 20 | 113.5 |
| 44 | (1):(5):(7):(19):(22) =1:1:0.36:0.46:0.68 | 21 | 115 |
| 45 | (2):(4):(7):(19):(22) =1:1:0.36:0.46:0.68 | 15 | 113.5 |
| 46 | (2):(5):(7):(19):(22) =1:1:0.36:0.46:0.68 | 20 | 113.5 |
| 47 | (1):(5):(7):(9):(19):(20):(22)=1:1:0.35:0.30:0.45:0.30:0.60 | 18 | 114.5 |
| 48 | (2):(4):(7):(9):(19):(20):(22)=1:1:0.35:0.30:0.45:0.30:0.60 | 13 | 112.5 |
| 49 | (2):(5):(7):(9):(19):(20):(22)=1:1:0.35:0.30:0.45:0.30:0.60 | 10 | 115 |

We claim:

1. A nematic liquid crystal composition comprising at least two cinnamic acid esters of the formula

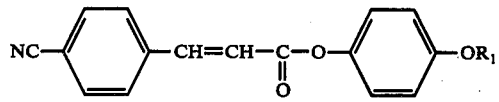

wherein $R_1$ is straight-chain alkyl of 4 to 8 carbon atoms.

2. A nematic liquid crystal composition comprising at least one cinnamic acid ester of the formula

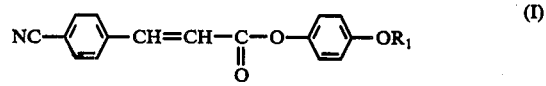

(I)

wherein $R_1$ is straight-chain alkyl of 4 to 8 carbon atoms, and at least one cinnamic acid ester of at least one of the formulae

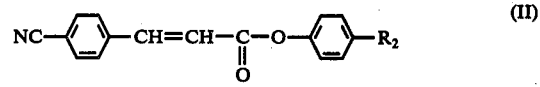

(II)

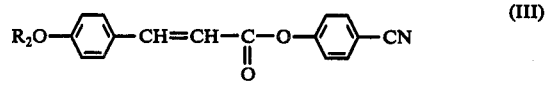

(III)

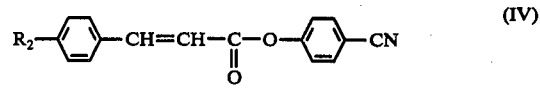

(IV)

wherein $R_2$ is straight-chain alkyl of 3 to 8 carbon atoms.

3. A nematic liquid crystal composition in accordance with claim 2 comprising at least one cinnamic acid ester of said formula (I) and at least one cinnamic acid ester of said formula (II).

4. A nematic liquid crystal composition in accordance with claim 2 comprising at least one cinnamic acid ester of said formula (I) and at least one cinnamic acid ester of said formula (III).

5. A nematic liquid crystal composition in accordance with claim 2 comprising at least one cinnamic acid ester of said formula (I) and at least one cinnamic acid ester of said formula (IV).

6. A nematic liquid crystal composition in accordance with claim 2 comprising at least one cinnamic acid ester of said formula (I), at least one cinnamic acid ester of said formula (II) and at least one cinnamic acid ester of said formula (IV).

* * * * *